United States Patent
Rose et al.

(10) Patent No.: US 11,000,631 B1
(45) Date of Patent: May 11, 2021

(54) METHODS FOR APPLYING A BIOACTIVE COATING ONTO A SURFACE OF AN IMPLANT

(71) Applicant: Smith & Nephew, Inc., Memphis, TN (US)

(72) Inventors: John Rose, Collierville, TN (US); Sied William Janna, Memphis, TN (US); Alisha Wilson Bergin, Olive Branch, MS (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 16/291,914

(22) Filed: Mar. 4, 2019

Related U.S. Application Data

(60) Provisional application No. 62/638,701, filed on Mar. 5, 2018, provisional application No. 62/638,991, filed on Mar. 6, 2018.

(51) Int. Cl.
*A61L 27/54* (2006.01)
*A61F 2/30* (2006.01)

(52) U.S. Cl.
CPC .......... *A61L 27/54* (2013.01); *A61F 2/30767* (2013.01); *A61F 2310/0097* (2013.01); *A61F 2310/00592* (2013.01); *A61L 2300/606* (2013.01); *A61L 2400/18* (2013.01); *A61L 2420/02* (2013.01)

(58) Field of Classification Search
None
See application file for complete search history.

(56) References Cited

U.S. PATENT DOCUMENTS 8,372,419 B2 * 2/2013 Hellerbrand ......... A61B 17/866
424/423

OTHER PUBLICATIONS

Trajkovski et al (Advanced Drug Delivery Reviews, 64, 1142-1151, 2012) Intra-operatively customized implant coating . . . .*
Amerstorfer et al. (the Journal of Arthroplasty, 32, 1618-1624, 2017) Superficial Vancomycin Coating of Bone . . . .*

\* cited by examiner

*Primary Examiner* — Tigabu Kassa
(74) *Attorney, Agent, or Firm* — Kacvinsky Daisak Bluni PLLC

(57) ABSTRACT

Devices, systems, and methods for applying a bioactive coating to an exterior surface of an implant are disclosed. In some embodiments, the bioactive coating may be applied to the surfaces of the implant within the operating room at the time of implantation. In one embodiment, the implant may be a temporary spacer used to temporary replace an implant in a patient suffering from an infection. The temporary spacer being, for example, an antibacterial material for fighting the infection. In some embodiments, the method includes providing a mold of the implant, and providing the bioactive coating within the mold. The method may further include inserting the implant into the mold so that the exterior surface of the implant contacts the bioactive coating, and then removing the implant from the mold.

8 Claims, 8 Drawing Sheets

METHODS FOR APPLYING A BIOACTIVE COATING ONTO A SURFACE OF AN IMPLANT

CROSS-REFERENCE TO RELATED APPLICATION

This application claims priority to, and the benefit of, pending U.S. provisional patent application No. 62/638,701, filed Mar. 5, 2018, entitled "Devices and Methods for Applying a Bioactive Coating Onto a Surface of an Implant" and claims priority to, and the benefit of, pending U.S. provisional patent application No. 62/638,991, filed Mar. 6, 2018, entitled "Devices and Methods for Applying a Bioactive Coating Onto a Surface of an Implant," the entire contents of which applications are incorporated by reference herein.

TECHNICAL FIELD

The present disclosure generally relates to medical devices, and more particularly, but not exclusively, relates to methods, systems, and devices for applying a bioactive coating onto surfaces of an implant. For example, in one embodiment, the present disclosure relates to methods, systems, and devices for applying a bioactive coating onto surfaces of a temporary spacer, the bioactive coating being applied to the spacer within a surgical environment such as, for example, an operating room.

BACKGROUND

It is commonly known to coat medical implants with one or more bioactive coatings. For example, it is known to coat the surfaces of an implant with a bioactive coating such as, for example, an antimicrobial coating, an antibacterial coating, a hydrogel, a paste, etc. The bioactive coating containing one or more biological compounds such as, for example, antimicrobials, antibiotics, growth factors, etc.

However, one problem with coated implants is that the lifespan of the coating may be shorter than the lifespan of the medical implant. Thus, it would be advantageous to provide a device, system, and/or method for applying a coating to the implant when needed, for example, in the operating room.

One known approach for applying a coating to the implant in, for example, the operating room is to use a syringe with a small spreader attached to the nozzle of the syringe to allow medical personnel to slowly dispense the coating over the required surfaces of the implant.

For a number of reasons, it would be beneficial to utilize a device, system, and method for applying a coating to the implant in, for example, the operating room that is faster and more accurate. As such, a need remains for further improvements in this technological field. The present disclosure addresses this need.

SUMMARY

The Summary is provided to introduce a selection of concepts in a simplified form, the concepts further described below in the Detailed Description. The Summary is not intended to identify key features or essential features of the claimed subject matter, nor is the Summary intended as an aid in determining the scope of the claimed subject matter.

A method for applying a bioactive coating to an exterior surface of an implant within an operating room at a time of implantation is disclosed. In one embodiment, the method may include providing a mold of the implant, providing, inserting, injecting, positioning, or the like (used interchangeably herein without the intent to limit) the bioactive coating within the mold, and inserting the implant into the mold so that the exterior surface of the implant contacts the bioactive coating. Thereafter, the implant may be removed from the mold and the implant including any bioactive coating adhered thereto may be implanted into a patient.

In another embodiment, the method may include providing an implant within an interior cavity of a mold, injecting the bioactive coating into a space between the exterior surface of the implant and an interior surface defining the interior cavity, and removing the implant from the mold.

In another embodiment, the method may include providing an annulus and, optionally, a delivery device, inserting the implant into an interior cavity of the annulus, and injecting the bioactive coating onto the implant via moving the annulus along a length of the implant.

In these and other embodiments, the implant may be a temporary spacer used in place of a permanent implant. For example, for patients suffering from an infection, a previously implanted implant may need to be replaced. In these situations, the temporary spacer may be coated with a bioactive coating within the operating room via any of the methods, devices, or systems described herein. The bioactive coating may include an antibacterial material used to fight the infection.

Embodiments of the present disclosure provide numerous advantages. For example, they provide an easy to use and effective system and method for coating an implant such as, for example, a temporary spacer, within an operating room at the time of implantation. As such, any risks associated with the shelf-life of the coating are alleviated.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

The accompanying drawings illustrate exemplary approaches of the disclosure, including the practical application of the principles thereof, as follows.

Figure 1:
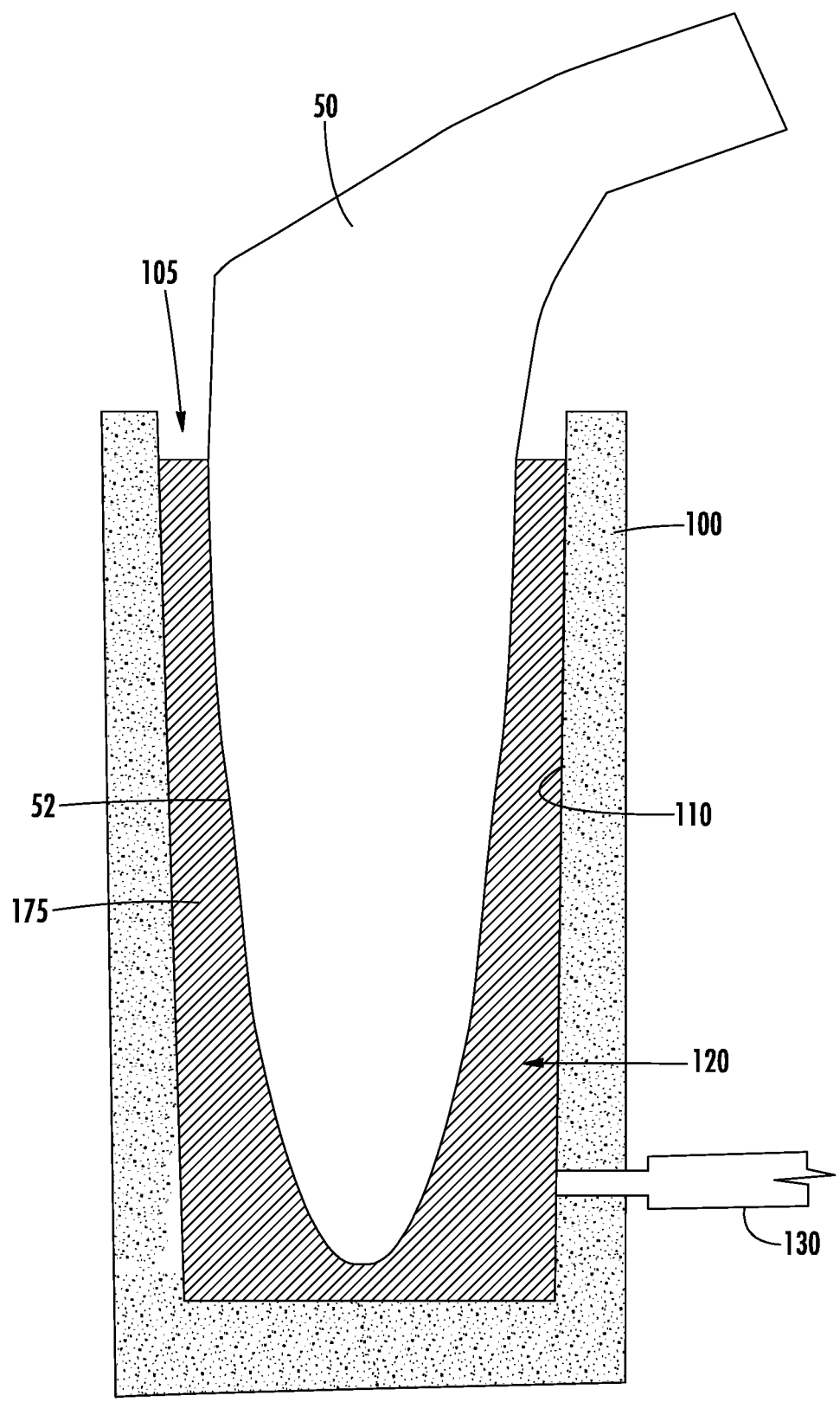
FIG. 1 illustrates a side, cross-sectional view of an example of an embodiment for coating an implant using a mold in accordance with one aspect of the present disclosure.

The drawings are not necessarily to scale. The drawings are merely representations, not intended to portray specific parameters of the disclosure. The drawings are intended to depict example embodiments of the disclosure, and therefore are not be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DESCRIPTION

For the purposes of promoting an understanding of the principles of the present disclosure, reference will now be made to example embodiments. It will nevertheless be understood that no limitation of the scope of the disclosure is thereby intended. Any alterations and further modifications in the described embodiments, and any further applications of the principles of the present disclosure as described herein are contemplated as would normally occur to one skilled in the art to which the disclosure relates.

The present disclosure is directed to devices, systems, and methods for allowing rapid and complete coverage of an implant with a bioactive coating. In some embodiments, devices, systems, and methods are arranged and configured to enable the bioactive coating to be applied within, for example, the operating room just prior to implantation of the implant. In one embodiment, the method may include providing a mold, and inserting a bioactive coating within an interior cavity of the mold. The method may further include inserting the implant into the interior cavity of the mold so that the exterior surface of the implant contacts the bioactive coating. Thereafter, the implant, and the coating applied thereto, may be removed from the mold.

As described herein, bioactive coatings may be any suitable coating now known or hereafter developed. For example, the bioactive coating may be a hydrogel or paste. Alternatively, and/or in addition, the bioactive coating may be an antibacterial or antibiotic coating. Alternatively, and/or in addition, the bioactive coating may include bioceramics, extracellular matrix proteins, biological peptides or growth factors imparting bioactivity and biocompatibility to the surface of the implant to promote bone ingrowth and differentiation of stem cells into osteoblasts leading to enhanced osteointegration of the implant. Furthermore, the bioactive coatings may include silver, nitric oxide, antiseptics and antimicrobial peptides with anti-microbial properties, which reduce bacterial adhesion and prosthetic infections.

Figure 2:
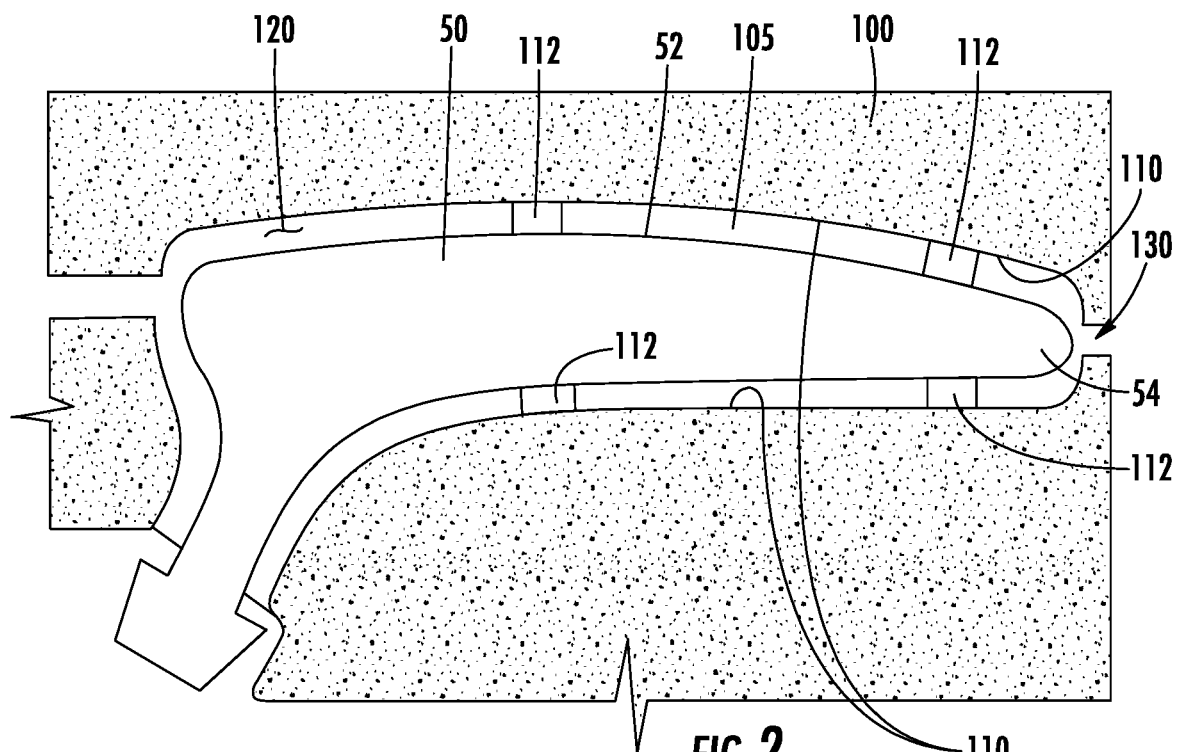
FIG. 2 illustrates a side, cross-sectional view of an example of an alternate embodiment for coating an implant using a mold and a delivery device in accordance with one aspect of the present disclosure.

Referring to FIGS. 1-4D, in one example embodiment, a receptacle or mold 100 (used interchangeably herein without the intent to limit) may be provided and/or made. The mold 100 may be manufactured as a single component (as schematically illustrated in FIG. 1) or may be manufactured from two or more components (as schematically illustrated in FIG. 2). In some embodiment, the mold 100 may include an interior cavity 105 that has a shape corresponding to that of the implant 50 to be coated, although such is not necessary. In some embodiments, the mold may be, for example, part of the packaging materials used for the implant 50, such as the tray that holds the implant 50 during, for example, delivery.

In use, the interior surfaces 110 of the mold 100 may generally follow the shape and/or contours of an exterior surface 52 of the implant 50 to be coated (as schematically illustrated in FIG. 2), although as schematically illustrated in FIG. 1, this is not necessary. In either event, a gap 120 between the interior surfaces 110 of the mold 100 and the exterior surfaces 52 of the implant 50 is created that may be filled with a bioactive coating 175 so that, when the implant 50 is inserted into the interior cavity 105 of the mold 100, the bioactive coating 175 resides between the interior surfaces 110 of the mold 100 and the exterior surfaces 52 of the implant 50.

As used herein, the implant 50 may be any suitable implant now known or hereafter developed. For example, in some embodiments, the implant 50 may be a femoral implant. In another embodiment, the implant 50 may be a knee implant, a hip implant, a spinal spacer, etc. In accordance with one particular aspect of the present disclosure, the implant 50 may be a temporary implant or spacer (used interchangeably herein without the intent to limit) made from, for example, bone cement (e.g., poly(methyl methacrylate)). The bioactive coating 175 may be, for example, an antibacterial coating used to fight infections. As will be appreciated by one of ordinary skill in the art, a temporary spacer may be temporary implanted into the patient, for example, when a previously implanted implant has been removed from a patient due to, for example, an infection. The temporary spacer may be temporary implanted into the patient while the patient fights the infection. Thereafter, the temporary spacer may be removed from the patient and a new, permanent implant may be implanted. Thus, for example, the spacer may be used, for example, in the event of an infection due to a previously inserted implant. After the existing implant and infected tissue are removed from the patient, the spacer is provided in its place. While implanted, the antibiotic coating may leach out of the spacer over a period of time. The spacer may then be removed and replaced with a permanent implant after the patient has adequately healed. The spacer may be coated with the bioactive coating 175 via any of the methods and devices described herein.

The temporary spacer and the bioactive coating may be arranged and configured to promote better adhesion between the bioactive coating and the spacer, and/or to provide better elution of the bioactive coating during use. For example, in one embodiment, the bioactive coating may include one or more additives to enable better adhesion to the spacer (e.g., the additives may enable better adhesion to the spacer as compared to a convenient implant). In addition, and/or alternatively, the spacer may include one or more surface features such as, for example, stipples or the like to assist with maintaining the antibiotic in place as the spacer is being implanted. In another embodiment, the spacer may be in the formed from a bone cement such as, for example, PMMA, and may contain an antibiotic material mixed therein. The spacer may further include one or more fissures or pockets formed on the surface of the spacer. These fissures or pockets could be loaded with an antibiotic coating and would provide an enhanced elution profile.

Referring to FIGS. 4A-4D, an example of a method for applying the bioactive coating 175 to the exterior surface 52 of the implant 50 according to one aspect of the present disclosure will be described in greater detail. Although non-limiting, the bioactive coating 175 may be applied by a dip coating process. Examples of other suitable application methods include, but are not limited to, spray coating, roll coating, electro coating, or combinations thereof.

As shown, at process (1) (FIG. 4A), the mold 100 is provided. The mold 100 may define an interior cavity 105. At process (2) (FIG. 4B), the interior cavity 105 of the mold 100 may be filled with the bioactive coating 175 such as, for example, the hydrogel or paste. In some embodiments, the bioactive coating 175 may be an antibacterial solution or material. In other embodiments, the bioactive coating 175 may be a powdered antibiotic. At process (3) (FIG. 4C), the implant 50 may be inserted into the interior cavity 105 of the mold 100. Once inserted, the bioactive coating 175 may be placed or positioned in direct contact with the exterior surfaces 52 of the implant 50. In some embodiments, the implant 50 may include a plurality of fissures, indentations, or recesses 58 formed in the exterior surface 52 of the implant 50 to provide an enhanced elution profile. As shown at process (4) (FIG. 4D), the volume of bioactive coating 175 may be displaced to substantially coat the exterior surfaces 52 of the implant 50 within the interior cavity 105 of the mold 100 to a given thickness. The implant 50 is then removed along with the bioactive coating 175, which adheres to the exterior surfaces 52 of the implant 50.

Figure 3:
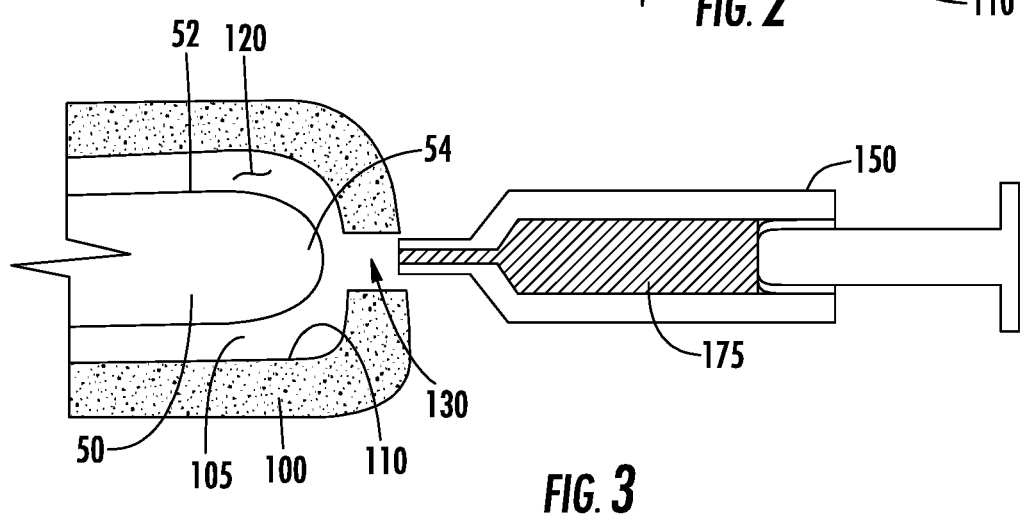
FIG. 3 illustrates a detailed, cross-sectional view of the example embodiment shown in FIG. 2.
Figure 4A:
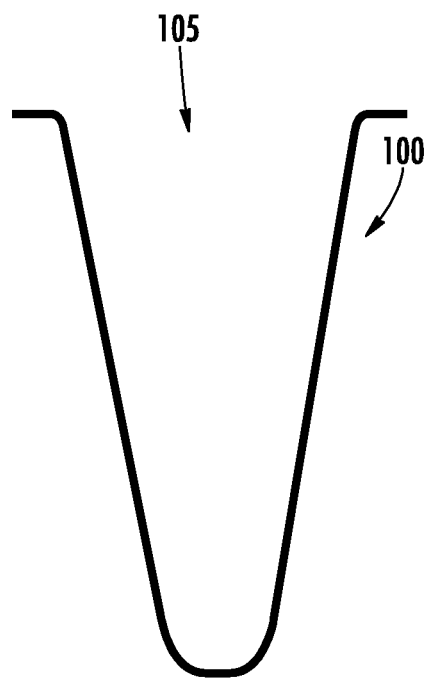
FIGS. 4A-4D illustrate various steps of an example process for coating an implant in accordance with one aspect of the present disclosure.
Figure 4B:
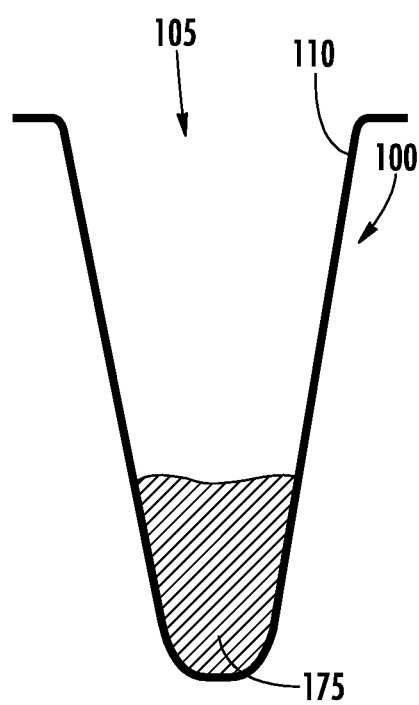
Figure 4C:
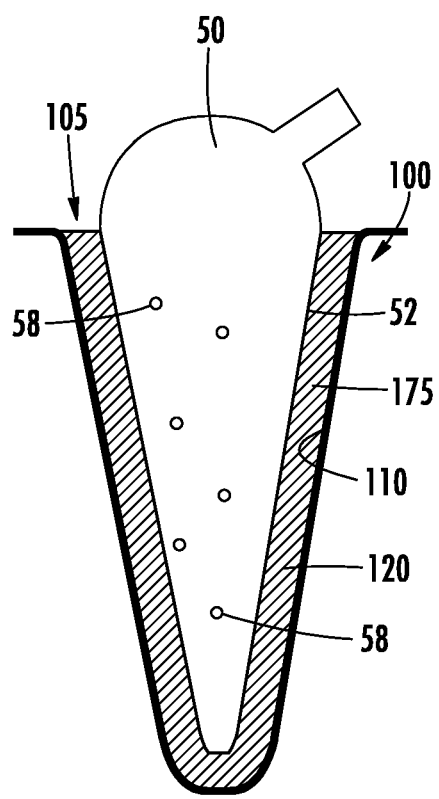
Figure 4D:
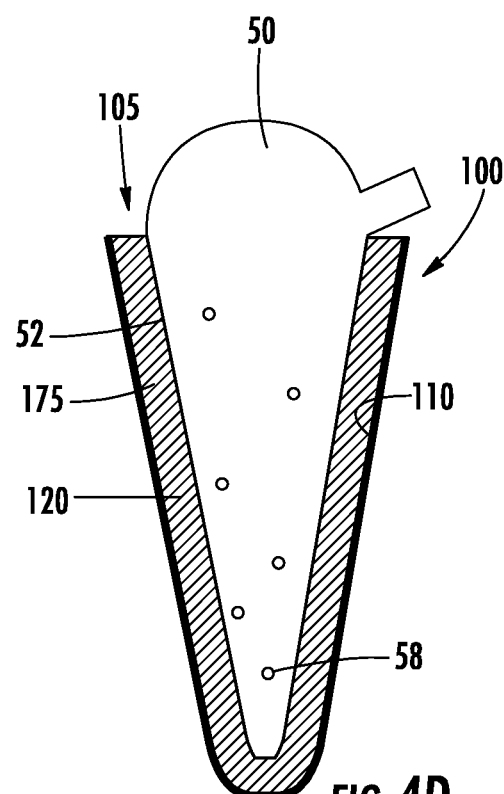

In an alternate embodiment, as schematically illustrated in FIGS. 2 and 3, the implant 50 may be inserted into the interior cavity 105 of the mold 100 and then the bioactive coating 175 may be inserted or injected into the gap or space 120 between the exterior surface 52 of the implant 50 and the interior surface 110 of the mold 100 via a delivery device 150, such as, for example, a syringe. The bioactive coating 175 may be injected through an injection port 130 formed in the mold 100. The injection port 130 is shown proximate a distal end 54 of the implant 50. However, the injection port 130, or multiple ports, may extend through the mold at different positions. Embodiments herein are not limited in this context.

As further shown in FIG. 2, in some embodiments, the mold 100 may include one or more surface features 112, such as ridges, projections, bumps, bearings, etc., on the interior surface 110 thereof to ensure that the implant 50 is properly positioned within the interior cavity 105 of the mold 100. The surface features 112 may ensure the gap 120 is present between the interior surfaces 110 of the mold 100 and the exterior surfaces 52 of the implant 50 so that, when the implant 50 is inserted into the mold 100, the bioactive coating 175 is evenly applied to the exterior surfaces 52 of the implant 50.

Figure 5A:
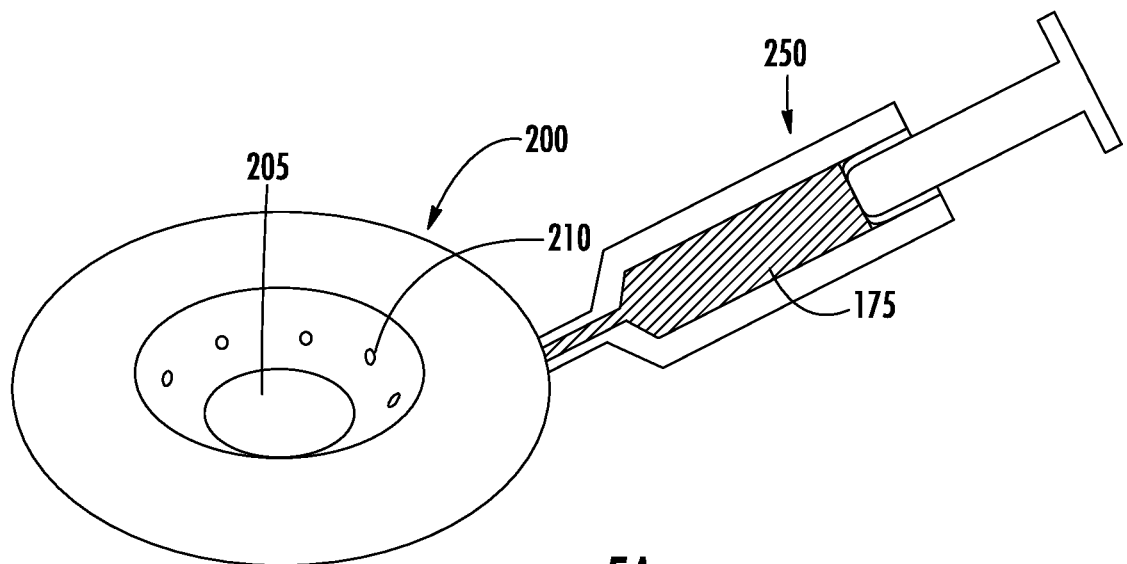
FIG. 5A illustrates a perspective view of an example of an embodiment for coating an implant using an annulus and a delivery device in accordance with one aspect of the present disclosure.
Figure 5B:
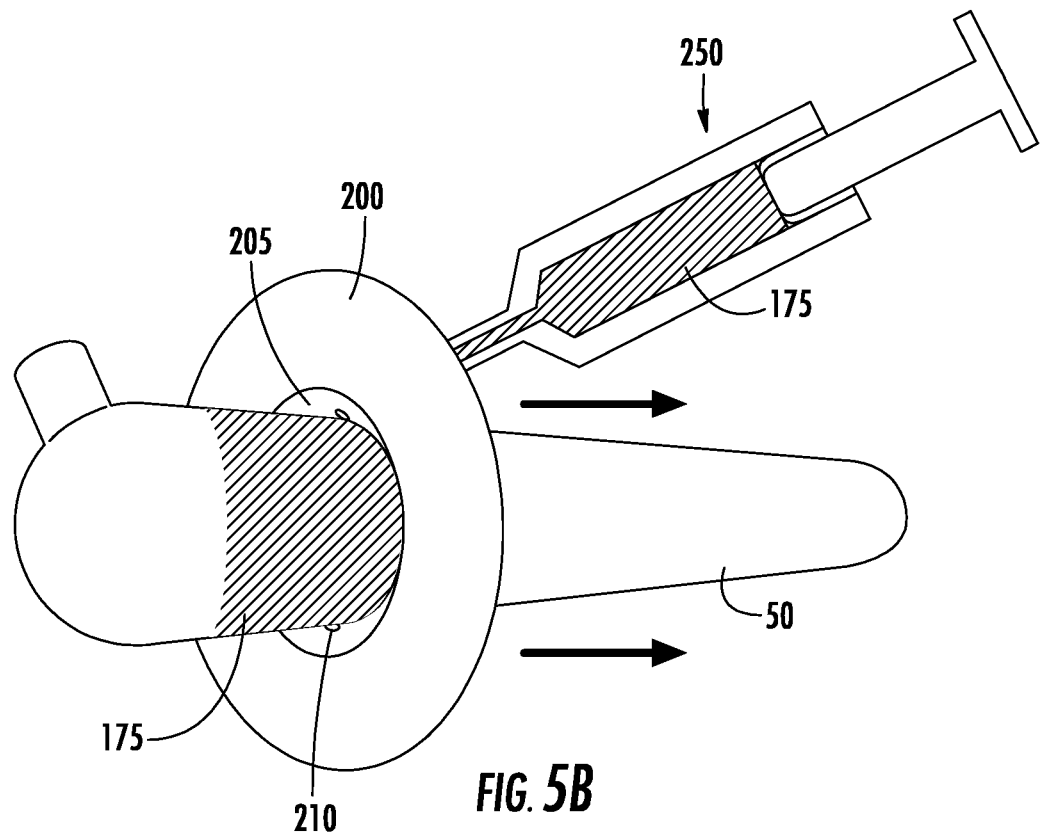
FIG. 5B illustrates a perspective view of the annulus shown in FIG. 5A coating an implant.

Referring to FIGS. 5A-5B, in another example embodiment, an annulus 200 may be used to coat the implant 50. For example, as shown, the annulus 200 may include an interior cavity 205 for receiving a portion of the implant 50 therein and one or more apertures 210, such as holes or slots on the surface thereof. For example, the apertures 210 may be positioned adjacent to, or in close proximity to, the interior cavity 205. In use, the annulus 200 may be connected to a delivery device 250 such as, for example, a syringe, containing the bioactive coating 175 so that the bioactive coating 175 may be injected into the annulus 200, through the apertures 210 formed in the annulus 200, and onto the implant 50 positioned within the interior cavity 205. The annulus 200 may be manufactured from any suitable material and/or manner now known or hereafter developed. For example, the annulus 200 may be flexible or rigid.

Figure 6A:
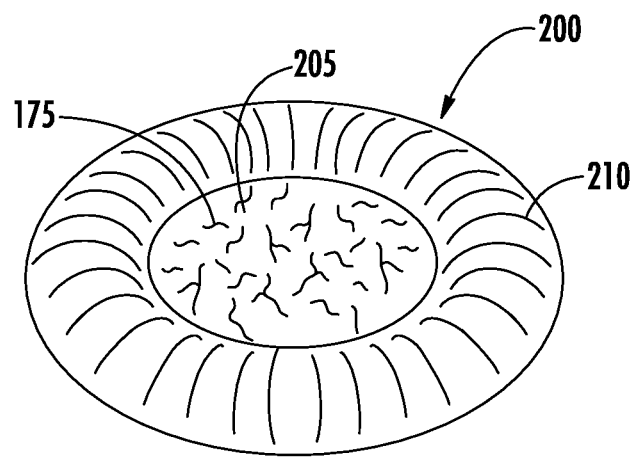
FIG. 6A illustrates a perspective view of an example of an embodiment for coating an implant using an annulus in accordance with one aspect of the present disclosure.
Figure 6B:
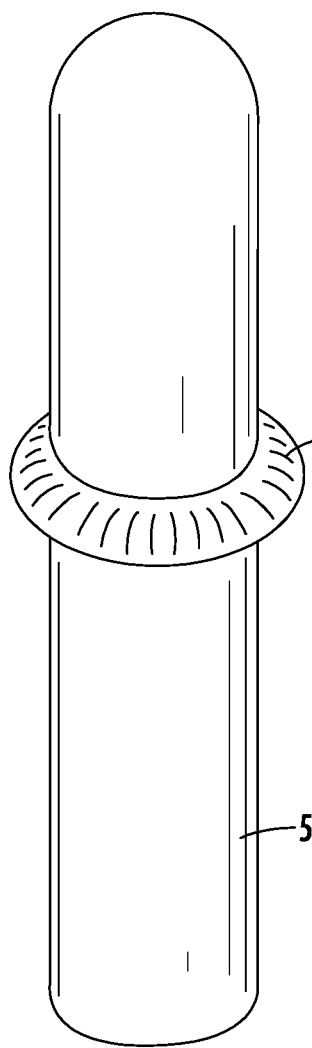
FIG. 6B illustrates a perspective view of the annulus shown in FIG. 6A coating an implant.
Figure 6C:
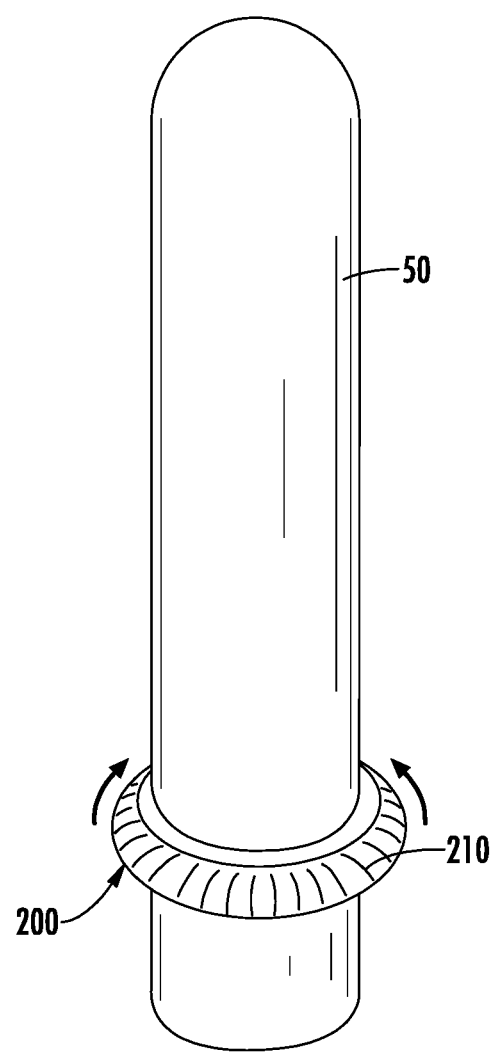
FIG. 6C illustrates a perspective view of the annulus shown in FIG. 6A coating an implant.

In use, an implant 50 such as, for example, a hip stem, may be positioned within the interior cavity 205 of the annulus 200. Next, as schematically illustrated in FIG. 5B, the annulus 200 may be moved along the length of the implant 50 while simultaneously injecting the bioactive coating 175 onto the implant 50. In other embodiments, as shown in FIGS. 6A-6C, the annulus 200 may be pre-filled with an adequate amount of bioactive coating 175 to render simultaneous injection via the delivery device 250 unnecessary. In use, the annulus 200 may be moved or slid along the length of the implant 50. Pressure applied by an operator as the annulus 200 is moving along the implant 50 may cause the bioactive coating 175 to secrete from the apertures 210.

Figure 7:
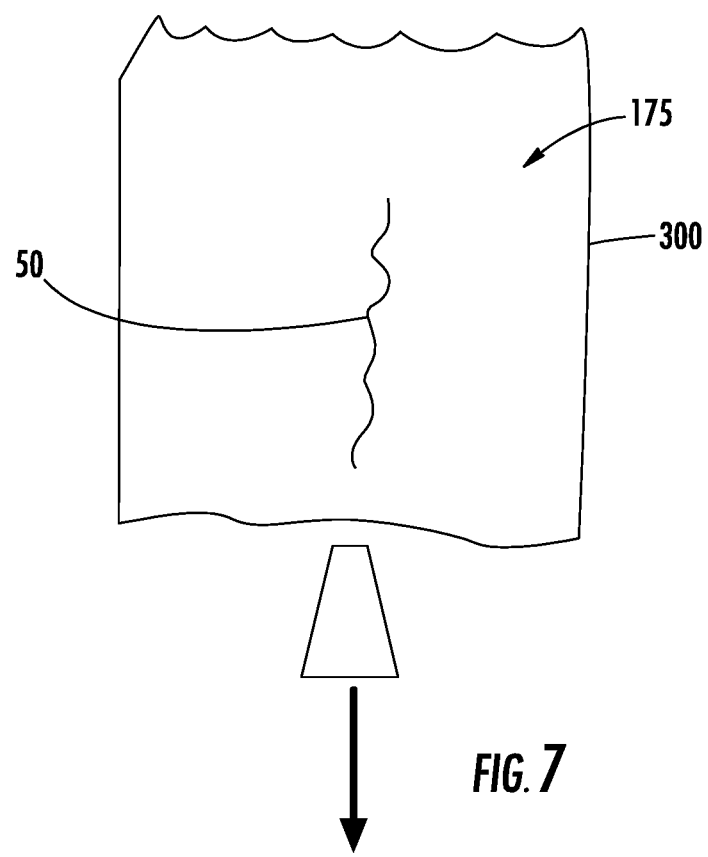
FIG. 7 illustrates a view of an example of an embodiment for coating an implant using a flexible container in accordance with one aspect of the present disclosure.

Referring to FIG. 7, in another example embodiment, a flexible container 300, such as a bag, may be used in place of the mold. In use, the bioactive coating 175 may be placed inside of the flexible container 300. Next, the implant 50 may be placed in the flexible container 300 and the bioactive coating 175 may be manipulated to coat the surfaces of the implant 50.

Figure 8:
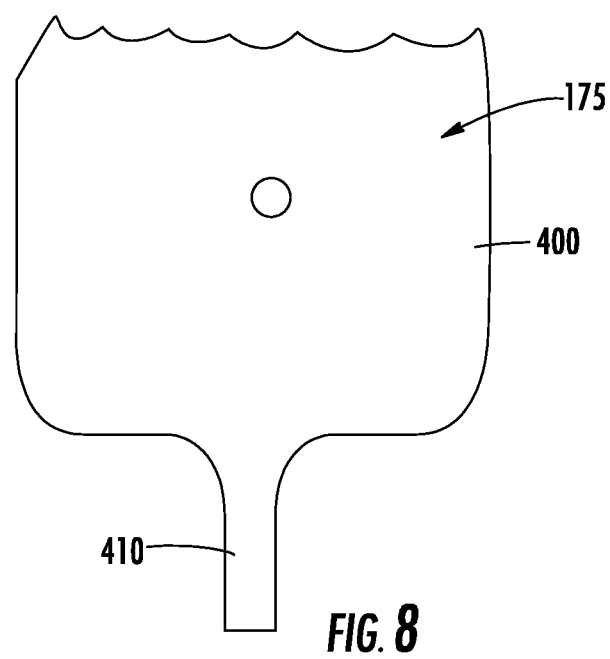
FIG. 8 illustrates a view of an example of an alternate embodiment for coating an implant using a flexible container in accordance with one aspect of the present disclosure.

Alternatively, referring to FIG. 8, an alternate example of an embodiment of a flexible container 400 may include a nozzle 410. In use, a bioactive coating 175 may be placed inside of the flexible container 400. The nozzle 410 may then be used to spread or coat the bioactive coating 175 over the exterior surfaces 52 of the implant 50. In some embodiments, the flexible container 400 may include more than one nozzle 410.

Referring to FIGS. 7 and 8, in an alternate embodiment, the bioactive coating 175 may be provided, for example, in a two-part solution and subsequently mixed within the flexible container 300, 400. For example, the bioactive coating 175 could be provided as a two-part mixture bagged together within the flexible container 300, 400 but separated by, for example, a breakable seam. In use, the seam could be broken bringing together the two solutions to form the bioactive coating 175. Alternatively, one solution may be located within the flexible container 300, 400 while the other may be injected inside of the flexible container 300, 400 just prior to or during use. In any event, the flexible container 300, 400 may then be manipulated to mix the solutions together. Finally, the flexible container 300, 400 may be used as a delivery mechanism to coat the implant 50.

Figure 9A:
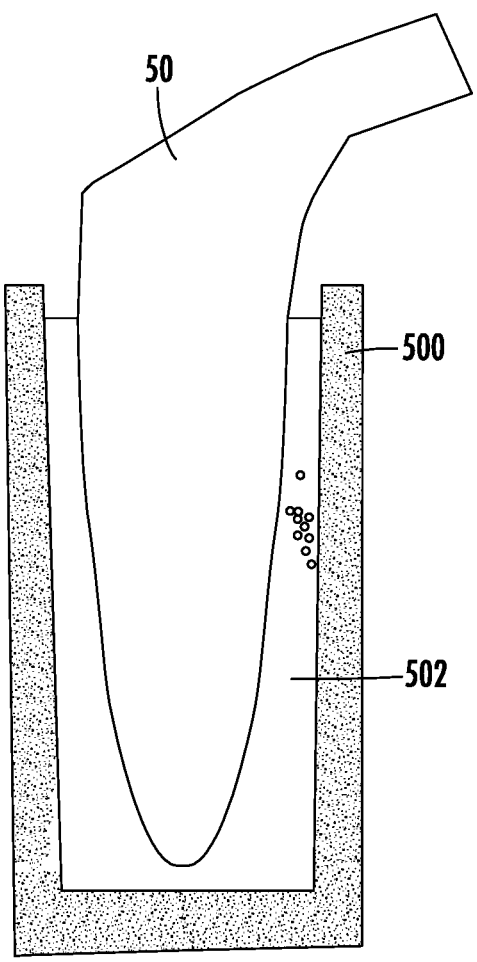
FIGS. 9A and 9B illustrate various steps of an example process for coating an implant in accordance with one aspect of the present disclosure.
Figure 9B:
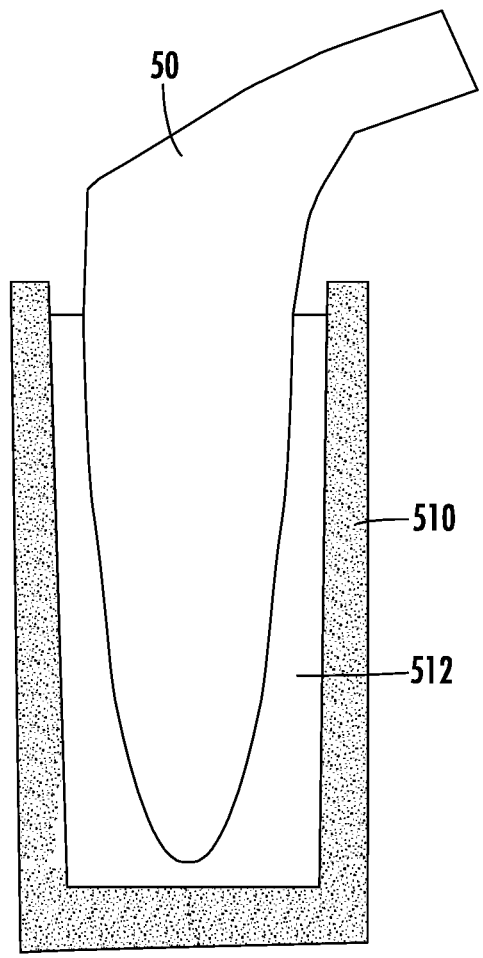

Referring to FIGS. 9A and 9B, in another embodiment, a bioactive coating 175 can be applied to the surfaces of the implant 50 in the operating room by, for example, wetting the surfaces of the implant 50. In use, the implant 50 may be wetted by any mechanism now known or hereafter developed, for example, in one embodiment, the implant 50 may be wetted using a water spray. Alternatively, as illustrated at process (1) (FIG. 9A), the implant 50 may be inserted into a first container 500 containing water 502 therein. Next, at process (2) (FIG. 9B), the implant 50 may be inserted into a second container 510 containing, for example, a powder 512 including the bioactive component such as, for example, a bioactive and de-hydrated gel. As a result, the powder 512 containing the bioactive and de-hydrated gel may adhere to the damp surfaces of the implant 50. Alternatively, the powder 512 could be sprinkled onto the damp surfaces of the implant 50. Next, the implant 50 and powder 512 may be inserted into saline or water to form the final gel coating.

Figure 10:
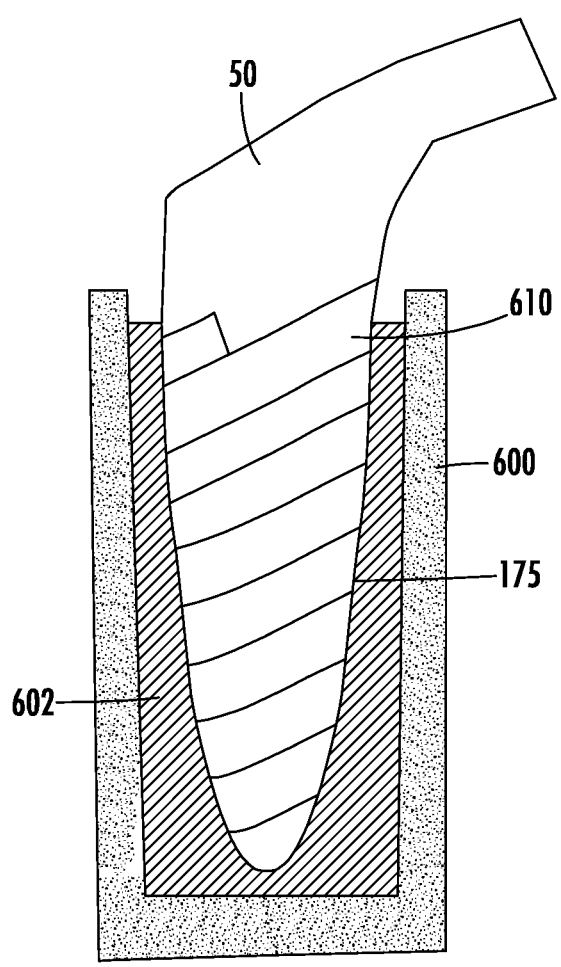
FIG. 10 illustrates a side, cross-sectional view of an example of an embodiment for coating an implant in accordance with one aspect of the present disclosure.

Referring to FIG. 10, in another embodiment, the implant 50 may be pre-coated with, for example, a de-hydrated hydrogel, which may be in the form of an adhesive, such as a tape 610. The implant 50 and the tape 610 may be immersed in a hydrating solution 602 (e.g., water or saline) positioned within an interior cavity of a receptacle or mold 600 to form a bioactive coating 175 such as, for example, a hydrogel, on the surface of the implant 50. In the embodiment shown, the tape 610 may be wrapped and/or applied to the implant 50 in, for example, the operating room. Once the tape 610 is applied to the implant 50, the implant 50 and the tape 610 may be placed in the interior cavity of the receptacle or mold 600 containing the hydrating solution 602 to form the bioactive coating 175 on the surface of the implant 50. In other embodiments, the hydrating solution 602 may be applied to the tape 610 in other ways, such as by spraying.

Although non-limiting, the tape 610 may be a biocompatible material, such as woven, non-woven, knitted, braided or crocheted, foam, sponge, or dendritic material. The tape 610 may also be a polymeric film or membrane or a mixture of two or more of these materials. Furthermore, the tape 610 may be porous or non-porous.

In one example embodiment, the bioactive coating (e.g., gel or paste) could be placed within a degradable, flexible container, such as flexible containers 300, 400 described above. The flexible container may be made from, for example, a rapidly degrading or soluble material which can be implanted into the patient together with the implant. The flexible container may degrade or dissolve once implanted. For example, the flexible container could degrade within approximately 2-3 hours of implantation. Embodiments are not limited in this context, however.

As used herein, bioactive coatings, such as bioactive coatings 175 may include a titanium substrate having silver deposited thereon, wherein the silver is operable to be eluted at an intended rate. As described in PCT Application No. PCT/US2017/014894, entitled Orthopaedic Implant, the entire content of which is hereby incorporated by reference, the silver deposited on the titanium substrate suitably includes silver ions and/or silver nanoparticles. The silver ions and/or silver nanoparticles may be dispersed either within or on top of a titanate nanostructure. In some embodiments, the bioactive coating may be a polymeric coating. For example, the implant may alternatively include a titanium substrate having silver deposited thereon, and further coated with a polymeric coating. Advantageously, adding a polymeric coating enables a controlled release of the silver from the implant into the body. This allows for a beneficial sustained controlled release of the silver and also reduces the cytotoxicity of large amounts of silver being released into the body. In some embodiments, the polymeric coating is biocompatible.

Non-limiting examples of suitable natural polymers include, but are not limited to, one or more of the following: hemaleucin; gelatin; starch; cellulose; chitosan; collagen; or combinations thereof. Suitably, the polymeric material may comprise hemaleucin, gelatin or a combination thereof. Non-limiting examples of suitable synthetic polymers include, but are not limited to, one or more of the following: polyesters such as, for example, polylactides (including poly-D-lactides, poly-L-lactides, poly~D,L-lactides and combinations thereof), poly glycosides, polylactide-polyglycolide copolymers (including poly-D-lactide-polyglycolide copolymers, poly-L- lactide-polyglycolide copolymers, poly-D,L-lactide-polyglycolide copolymers and combinations thereof) and polyester-polyethylene glycol (PEG) copolymers; poiyorthoesters; polyarnino acids; polyurethanes; or combinations thereof. Suitably, the polymeric material may comprise poly-D,L actide-polyglycolide copolymers, poly-D,L-lactides or a combination thereof.

As used herein, examples of hydrogels which may be used according to embodiments of the present disclosure may be collagen (particularly Type 1), fibrin, TETRONICS™ and POLOXAMINES™, which are poly(oxyethylene)-poly (oxypropylene) block copolymers of ethylene diamine; polysaccharides, chitosan, poly(vinyl amines), poly(vinyl pyridine), poly(vinyl imidazole), polyethylenimine, poly-L-lysine, growth factor binding or cell adhesion molecule binding derivatives, derivatised versions of the above, e.g. polyanions, polycations, peptides, polysaccharides, lipids, nucleic acids or blends, block-copolymers or combinations of the above or copolymers of the corresponding monomers; agarose, methylcellulose, hydroxyproylmethylcellulose, xyloglucan, acetan, carrageenan, xanthan gum/locust beangum, gelatine, collagen (particularly Type 1), PLURONICS™, POLOXAMERS™, POLY(N-isopropylacrylmide) and N-isopropylacrylmide copolymers.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other.

Furthermore, identification references (e.g., primary, secondary, first, second, third, fourth, etc.) are not intended to connote importance or priority, but are used to distinguish one feature from another. The drawings are for purposes of illustration only and the dimensions, positions, order and relative sizes reflected in the drawings attached hereto may vary.

Furthermore, the terms "substantial" or "substantially," as well as the terms "approximate" or "approximately," can be used interchangeably in some embodiments, and can be described using any relative measures acceptable by one of ordinary skill in the art. For example, these terms can serve as a comparison to a reference parameter, to indicate a deviation capable of providing the intended function. Although non-limiting, the deviation from the reference parameter can be, for example, in an amount of less than 1%, less than 3%, less than 5%, less than 10%, less than 15%, less than 20%, and so on.

Still furthermore, although the illustrative methods are described above as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure. Furthermore, the methods may be implemented in association with the formation and/or processing of structures illustrated and described herein as well as in association with other structures not illustrated.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, the present disclosure has been described herein in the context of a particular implementation in a particular environment for a particular purpose. Those of ordinary skill in the art will recognize the usefulness is not limited thereto and the present disclosure may be beneficially implemented in any number of environments for any number of purposes. Thus, the claims set forth below are to be construed in view of the full breadth and spirit of the present disclosure as described herein.

What is claimed is:

1. A method for applying a bioactive coating to an exterior surface of an implant spacer within an operating room at a time of implantation, the method comprising:
   providing a mold having an interior cavity, wherein the mold is part of packaging materials used for delivering the implant spacer;
   inserting the implant spacer into the interior cavity of the mold, wherein one or more projections extend from an internal surface of the interior cavity of the mold and into contact with an exterior surface of the implant spacer to space the implant spacer from the internal surface of the mold to enable positioning of the implant spacer within the interior cavity of the mold;
   positioning the bioactive coating within the interior cavity of the mold, wherein the bioactive coating comprises an antibiotic coating, wherein positioning the bioactive coating within the interior cavity of the mold comprises: injecting, after inserting the implant spacer into the cavity of the mold, the bioactive coating into a space between the exterior surfaces of the implant spacer and the interior surface defining the interior cavity of the mold; and
   removing the implant spacer from the interior cavity of the mold along with the bioactive coating adhered thereto.

2. The method of claim 1, further comprising forming a plurality of recesses in the exterior surface of the implant spacer prior to inserting the implant spacer into the mold.

3. The method of claim 1, wherein the implant spacer is formed from a bone cement.

4. The method of claim 1, further comprising coating the implant spacer with a liquid prior to inserting the implant spacer into the interior cavity of the mold, wherein the bioactive coating is a powdered antibiotic, and wherein the liquid causes the powdered antibiotic to adhere to the exterior surface of the implant spacer.

5. The method of claim 1, further comprising:
   removing a previously inserted implant from a patient; and
   implanting the implant spacer along with the bioactive coating adhered thereto into the patient.

6. The method of claim 5, wherein the implant spacer is a temporary spacer, the temporary spacer is formed from a bone cement and the antibiotic coating fights infection.

7. The method of claim 6, wherein the antibiotic coating leaches out of the temporary implant spacer over a period of time.

8. The method of claim 6, wherein the temporary implant spacer and the bioactive coating are arranged and configured to promote better adhesion between the bioactive coating and the temporary implant spacer and to provide better elution of the bioactive coating.

* * * * *